United States Patent
Zhang et al.

(10) Patent No.: US 12,275,936 B2
(45) Date of Patent: Apr. 15, 2025

(54) METHOD TO CONNECT CHROMATIN ACCESSIBILITY AND TRANSCRIPTOME

(71) Applicant: The Regents of the University of California, Oakland, CA (US)

(72) Inventors: Kun Zhang, La Jolla, CA (US); Song Chen, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 953 days.

(21) Appl. No.: 17/044,128

(22) PCT Filed: Apr. 18, 2019

(86) PCT No.: PCT/US2019/028042
§ 371 (c)(1),
(2) Date: Sep. 30, 2020

(87) PCT Pub. No.: WO2019/204560
PCT Pub. Date: Oct. 24, 2019

(65) Prior Publication Data
US 2021/0123044 A1    Apr. 29, 2021

Related U.S. Application Data

(60) Provisional application No. 62/659,210, filed on Apr. 18, 2018.

(51) Int. Cl.
*C12N 15/10*    (2006.01)
*C12Q 1/6876*    (2018.01)

(52) U.S. Cl.
CPC ....... *C12N 15/1065* (2013.01); *C12Q 1/6876* (2013.01); *C12Q 2600/158* (2013.01)

(58) Field of Classification Search
CPC .............. C12N 15/1065; C12Q 1/6876; C12Q 2600/158
USPC .......................................................... 506/2
See application file for complete search history.

(56) References Cited

U.S. PATENT DOCUMENTS

2008/0293589 A1    11/2008    Shapero
2018/0023133 A1    1/2018    Rotem et al.

FOREIGN PATENT DOCUMENTS

WO    WO-2019157529 A1 *    8/2019    ....... C07K 14/70539

OTHER PUBLICATIONS

Perri et al. Epigenetic control of gene expression: Potential implications for cancer treatment. Critical Reviews in Oncoloy/Hematology. 111, 2017, 166-172. (Year: 2017).*
Buenrostro et al. ATAC-seq: A method for assaying chromatin accessibility genome-wide. Curr Protoc Mol Biol. 109, 2015, 21.29.1-21.29.9. (Year: 2015).*

(Continued)

*Primary Examiner* — Aaron A Priest
*Assistant Examiner* — Randi Lynn Beil
(74) *Attorney, Agent, or Firm* — Eversheds-Sutherland (US) LLP

(57) ABSTRACT

The invention provides scalable methods for measuring chromatin accessibility and RNA expression in the same single cells by connecting chromatin accessibility and transcriptome. Specifically, the disclosure provides a methods for concurrent characterization of gene expression levels and epigenetic landscape within a single cell comprising determining chromatin accessibility and RNA expression in the cell with a splint oligonucleotide.

8 Claims, 13 Drawing Sheets

(56) References Cited

OTHER PUBLICATIONS

Goldberg et al. Epigenetics: A landscape takes shape. Cell. 128, 2007, 635-638. (Year: 2007).*

Macosko et al. Highly parallel genome-wide expression profiling of individual cells using nanoliter droplets. Cell. 161, 2015, 1202-1214. (Year: 2015).*

Illumina. Illumina adapter sequences. Data Sheet [online]. 2015. [retrieved Sep. 23, 2023]. <URL:https://dnatech.genomecenter.ucdavis.edu/wp-content/uploads/2013/06/illumina-adapter-sequences_1000000002694-00.pdf> (Year: 2015).*

Chang et al. TAIL-seq: Genome-wide determination of poly(A) tail length and 3' end modifications. Molecular Cell. 53, 2014, 1044-1052. (Year: 2014).*

PCT International Search Report and Written Opinion for PCT Application No. PCT/US2019/028042 mailed Aug. 20, 2019 (20 pages).

Bajic et al., "Identification of Open Chromatin Regions in Plant Genomes Using ATAC-Seq," Methods Mol Biol., 2018, 1675:183-201.

Dhar et al., "Research Highlights: Microfluidic-Enabled Single-Cell Epigenetics," Lab Chip, 2015, 15:4109-4113.

Goldberg et al., "Epigenetics: A Landsapae Takes Shape," Cell, 2007, 128:635-638.

Jalkanen et al., "Determinants and Implications of mRNA Poly(A) Tail Size—Does this Protein Make My Tail Look Big?," Semin Cell Dev Biol., 2014, 0:24-32.

Karlic et al., "Histone Modification Levels are Predictive for Gene Expression," PNAS, 2010, 2926-2931.

Marco et al., "Bifurcation Analysis of Single-Cell Gene Expression Data Reveals Epigenetic Landscape," PNAS, 2014, E5643-E5650.

Smith et al., "Highly-Multiplexed Barcode Sequencing: An Efficient Method for Parallel Analysis of Pooled Samples," Nucleic Acids Research, 2010, 38(13):e142.

Sos et al., "Characterization of Chromatin Accessibility with a Transposome Hypersensitive Sites Sequencing (THS-seq) Assay," Genome Biology, 2016, 17:20.

* cited by examiner

METHOD TO CONNECT CHROMATIN ACCESSIBILITY AND TRANSCRIPTOME

CROSS REFERENCE TO RELATED APPLICATIONS

This application claims the priority benefit of U.S. Provisional Application No. 62/659,210, filed Apr. 18, 2018, which application is incorporated herein by reference.

STATEMENT OF GOVERNMENT INTEREST

The invention was made with support from the National Institutes of Health under Grant No. HL123755. The government has certain rights in the invention.

BACKGROUND

The genome is generally replicated with high-fidelity, but stochastic somatic alterations occur as a consequence of inherited mutations, environmental factors, or inaccurately resolved errors in transcription or replication. These genetic changes accumulate over time, thus complicating the elucidation and understanding of genomes and transcriptomes and the factors, such as chromatin accessibility, influencing them, because most genome-wide assays are sequencing-based that yield genome-wide data, but at the cost of averaging across large cell populations and ignoring genetic variability at the level of individual cells.

Advances in single-cell assays promise to overcome this limitation. Single-cell sequencing provides information that is not affected by heterogeneity of bulk samples. Sequencing of one molecular type (RNA, methylated DNA, or open chromatin) in a single cell, provides specific insights into that cell's phenotype and links to its specific epigenetic regulation landscape. The regulatory effect of individual influencing factors, such as chromatin accessibility, can be assessed. By taking measurements of these phenotypes and factors from the same single cells, inferences can be made unambiguously and unaffected by the genetic variability of large cell populations.

Although, single-cell characterization of chromatin accessibility and RNA expression has been demonstrated by a variety of methods, no existing method can simultaneously perform both measurements in the same cells at scale.

Previous multi-omics measurement using single cell technology generally rely on manual separation of materials into individual tubes and paralleled sequencing, which not only greatly limits their scalability, but can also lead to material loss, which can be significant due to the very limited starting material inside single cells.

New scalable methods for performing multi-omic single cell assays are needed. Additionally, new methods for performing multi-omic single cell assays, that can be performed simultaneously and without the need for separation of the starting material inside single cells into multiple tubes, are needed.

SUMMARY OF THE INVENTION

The present invention provides a method to connect chromatin accessibility and transcriptome in order to enable measuring of chromatin accessibility and RNA expression in the same single cells at a very high throughput.

In embodiments, the invention provides a method using a micro-droplet based protocol, wherein a splint oligo is used to allow the capture of chromatin accessible regions, as well as mRNA from the same single cells by barcoded oligo-dT beads.

In embodiments, the present invention is used for comprehensive characterization of both the epigenetic regulation landscape and the transcriptome profile.

In embodiments, the present invention is used to study epigenetic control of gene expression.

In other embodiments, the present invention is used to uncover cellular heterogeneity in healthy or diseases tissues, including tumors.

These and other aspects of the present invention will be apparent to those of ordinary skill in the art in the following description, claims and accompanying figures.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying figures of which:

FIG. 1a show a workflow of SNARE-seq. Key steps are outlined in the main text. FIG. 1b shows an aggregate single-nucleus chromatin accessibility profiles recaptured published profiles of ATAC-seq and Omni-ATAC in GM12878 cells. FIG. 1c shows a t-SNE visualization of SNARE-seq gene expression (upper panel) and chromatin accessibility (lower panel) data from BJ, GM12878, H1 and K562 cell mixture. Cellular identities are colored based on independent clustering results with either expression or chromatin data. FIG. 1d shows an inter-assay identity agreement reveals consistent linked transcriptome and chromatin accessibility profiles of SNARE-seq data. The size and color depth of each circle represents the number of cellular barcodes that were identified by the different assays.

FIG. 2a shows UMAP projection of SNARE-seq expression data of mouse cerebral cortex nuclei. Cell types were assigned based on known markers. FIG. 2b shows a heatmap showing the normalized expression of cell type-specific genes relative to the maximum expression level across all cell types. FIG. 2c shows UMAP projection of SNARE-seq chromatin accessibility data of mouse cerebral cortex nuclei. Cells are labeled with the same color codes for cell types identified by the linked expression data. FIG. 2d shows a heatmap showing the normalized chromatin accessibility of type-specific accessible sites relative to the maximum accessibility across all cell types. FIG. 2e shows chromatin accessibility tracks generated from cell-type specific or batch aggregated chromatin accessibility data at pericyte (left) and microglia (right) marker gene loci (Vtn and CD45respectively). For better visualization, the promoter regions were shaded in gray. FIG. 2f shows pseudotime trajectories constructed with SNARE-seq expression (upper panels) and chromatin accessibility (lower panels) profiles for 1,469 nuclei (214 IP-Hmgn2, 99 IP-Gadd45g, 437 IP-Eomes, 177 Ex-L2/3-Cntn2 and 542 Ex-L2/3-Cux1) from the mouse cerebral cortex. Cells are colored according to pseudotime score (left panels) or cellular identities (right panels). FIG. 2g shows a promoter accessibility (yellow) and gene expression (red) changes of Sox6, Gpm6b, Nrxn1 and Khdrbs2 across pseudotime during early neurogenesis.

DETAILED DESCRIPTION

Figure 1A:
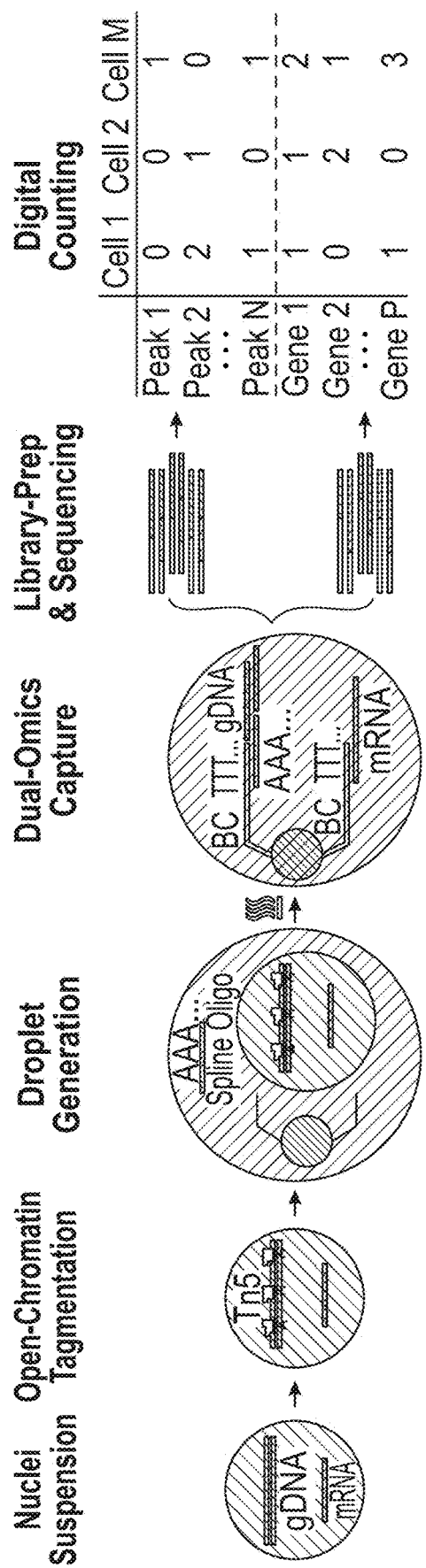
FIGS. 1a-1d show linked single-nucleus transcriptome and chromatin accessibility sequencing of human cell mixtures.

The materials, compounds, compositions, articles, and methods described herein may be understood more readily by reference to the following detailed description of specific aspects of the disclosed subject matter and the Examples and Figures included therein.

All publications, patents, and patent applications mentioned in this specification are herein incorporated by reference to the same extent as if each individual publication, patent, or patent application was specifically and individually indicated to be incorporated by reference. Where a publication has more than one edition, the most recent published edition thereof as of the priority filing date herein is intended.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligonucleotide or polynucleotide chemistry and hybridization described herein are those well-known and commonly used in the art. Standard techniques are used for recombinant DNA, oligonucleotide synthesis, tissue culture and cell transformation. Enzymatic reactions and purification techniques are performed using commercially available kits according to manufacturer's specifications or as commonly accomplished in the art or as described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as Molecular Cloning: A Laboratory Manual, most recent edition (Sambrook et al., 1989) Cold Spring Harbor Press; Oligonucleotide Synthesis (M J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C A. Janeway and P. Travers, 1997); Antibodies (P. Finch, 1997); Antibodies: apractical approach (D. Catty., ed., IRL Press, 1988-1989); Monoclonal antibodies: apractical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

"Amplification" refers to any known procedure for obtaining multiple copies of a target nucleic acid or its complement, or fragments thereof. The multiple copies may be referred to as amplicons or amplification products. Amplification, in the context of fragments, refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), reverse transcription polymerase chain reaction (RT-PCR), ligase chain reaction (LCR), strand-displacement amplification (SDA), and transcription-mediated or transcription-associated amplification.

"Complementary" means that a contiguous nucleic acid base sequence is capable of hybridizing to another base sequence by standard base pairing (hydrogen bonding) between a series of complementary bases. Complementary sequences may be completely complementary (i.e. no mismatches in the nucleic acid duplex) at each position in an oligomer sequence relative to its target sequence by using standard base pairing (e.g., G:C, A:T or A:U pairing) or sequences may contain one or more positions that are not complementary by base pairing (e.g., there exists at least one mismatch or unmatched base in the nucleic acid duplex), but such sequences are sufficiently complementary because the entire oligomer sequence is capable of specifically hybridizing with its target sequence in appropriate hybridization conditions (i.e. partially complementary). Contiguous bases in an oligomer are typically at least 80%, preferably at least 90%, and more preferably completely complementary to the intended target sequence.

"Configured to" denotes an actual arrangement of a nucleic acid sequence configuration of a referenced oligonucleotide. For example, a primer that is configured to generate a specified amplicon from a target nucleic acid has a nucleic acid sequence that hybridizes to the target nucleic acid or a region thereof and can be used in an amplification reaction to generate the amplicon. Also as an example, an oligonucleotide that is configured to specifically hybridize to a target nucleic acid or a region thereof has a nucleic acid sequence that specifically hybridizes to the referenced sequence under stringent hybridization conditions.

"Configured to specifically hybridize to" means that an oligonucleotide is designed to have a nucleic acid sequence that can hybridize with a target nucleic acid or region thereof. The oligonucleotide is designed to function as a component of an assay for amplification and detection of a target nucleic acid (or a region thereof) in a sample, and therefore is designed to hybridize with a target nucleic acid (or a region thereof) in the presence of other nucleic acids that may be found in testing samples.

"Fragment" refers to a piece of contiguous nucleic acid that contains fewer nucleotides than the complete nucleic acid.

"Hybridization" or "annealing" refer to the base-pairing interaction of one nucleic acid with another nucleic acid (typically an antiparallel nucleic acid) that results in formation of a duplex or other higher-ordered structure (i.e. a hybridization complex). The primary interaction between the antiparallel nucleic acid molecules is typically base specific, e.g., A/T and G/C. It is not a requirement that two nucleic acids have 100% complementarity over their full length to achieve hybridization. Nucleic acids hybridize due to a variety of well characterized physio-chemical forces, such as hydrogen bonding, solvent exclusion, base stacking and the like. An extensive guide to the hybridization of nucleic acids is found in Tijssen (1993) Laboratory Techniques in Biochemistry and Molecular Biology--Hybridization with Nucleic Acid Probes part I chapter 2, "Overview of principles of hybridization and the strategy of nucleic acid probe assays," (Elsevier, New York), as well as in Ausubel (Ed.) Current Protocols in Molecular Biology, Volumes I, II, and III, 1997, which is incorporated by reference.

"Nucleic acid" or "nucleic acid molecule" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof.

A nucleic acid backbone can be made up of a variety of linkages, including one or more of sugar-phosphodiester linkages, peptide-nucleic acid bonds, phosphorothioate linkages, methylphosphonate linkages, or combinations thereof. Sugar moieties of the nucleic acid can be ribose, deoxyribose, or similar compounds having known substitutions (e.g. 2'-methoxy substitutions and 2'-halide substitutions). Nitrogenous bases can be conventional bases (A, G, C, T, U) or analogs thereof (e.g., inosine, 5-methylisocytosine, isoguanine). A nucleic acid can comprise only conventional sugars, bases, and linkages as found in RNA and DNA, or can include conventional components and substitutions (e.g., conventional bases linked by a 2'-methoxy backbone, or a nucleic acid including a mixture of conventional bases and one or more base analogs). Nucleic acids can include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA). Nucleic acids can include modified bases to alter the function or behavior of the nucleic acid (e.g., addition of a 3'-terminal dideoxynucleotide to block additional nucleotides from being added to the nucleic acid). Synthetic methods for making nucleic acids in vitro are well known in the art although nucleic acids can be purified from natural sources using routine techniques. Nucleic acids can be single-stranded or double-stranded.

An "isolated" nucleic acid as used herein refers to a component that is removed from its original environment (for example, its natural environment if it is naturally occurring or a reaction mixture if it is synthetic). An isolated nucleic acid typically contains less than about 50%, preferably less than about 75%, and most preferably less than about 90%, of the components with which it was originally associated. "Primer" refers to an enzymatically extendable oligonucleotide, generally with a defined sequence that is designed to hybridize in an antiparallel manner with a complementary, primer-specific portion of a target nucleic acid. A primer can initiate the polymerization of nucleotides in a template-dependent manner to yield a nucleic acid that is complementary to the target nucleic acid when placed under suitable nucleic acid synthesis conditions (e.g. a primer annealed to a target can be extended in the presence of nucleotides and a DNA/RNA polymerase at a suitable temperature and pH). Suitable reaction conditions and reagents are known to those of ordinary skill in the art. A primer is typically single stranded for maximum efficiency in amplification, but may alternatively be double stranded. If double stranded, the primer is generally first treated to separate its strands before being used to prepare extension products. The primer generally is sufficiently long to prime the synthesis of extension products in the presence of the inducing agent (e.g. polymerase). Specific length and sequence will be dependent on the complexity of the required DNA or RNA targets, as well as on the conditions of primer use such as temperature and ionic strength. Preferably, the primer is about 5-100 nucleotides. Thus, a primer can be, e.g., 5, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95 or 100 nucleotides in length. A primer does not need to have 100% complementarity with its template for primer elongation to occur; primers with less than 100% complementarity can be sufficient for hybridization and polymerase elongation to occur. A primer can be labeled if desired. The label used on a primer can be any suitable label, and can be detected by, for example, spectroscopic, photochemical, biochemical, immunochemical, chemical, or other detection means. A labeled primer therefore refers to an oligomer that hybridizes specifically to a target sequence in a nucleic acid, or in an amplified nucleic acid, under conditions that promote hybridization to allow selective detection of the target sequence.

"Barcoded oligo primer" refers to a primer having a specific unique molecular identifier (UMI) to label an individual molecule and a shared cellular barcode (Cell Barcode in FIG. 3 for example) to indicate the cellular identity of those molecules from the same cell. After sequencing, reads can be counted and/or sorted into sample libraries via detection of the appropriate barcode. "Barcoded oligo-dT primer" refers to a primer having a cellular barcode and a UMI followed by a string of deoxythymine (dT) which is used for the capture of the target sequences.

"Splint oligo" refers to an enzymatically extendable oligonucleotide, generally with a defined sequence that is configured to hybridize in an antiparallel manner with complementary, oligo-specific portion of two target nucleic acids in such a manner that the terminal 3'-hydroxyl group of a first target nucleic acid is joined to the 5'-phosphate group of a second nucleic acid in the presence of the oligo splint.

"Sample preparation" refers to any steps or methods that prepare a sample for subsequent sequencing, amplification, and/or detection of target nucleic acids present in the sample. Sample preparation may include any known method of concentrating components, such as nucleic acids, from a larger sample volume. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically captures a target nucleic acid and separates it from other sample components.

"Sequencing" refers to any known procedure, method, or technology for determining the precise order of the nucleosides or nucleoside analogs of a target nucleic acid molecule, or its complement, or fragments thereof. Sequencing, in the context of fragments, refers to determining the precise order of nucleosides or nucleotides within a nucleic acid molecule that contains less bases than the complete target nucleic acid molecule e.g., determined by sequencing amplicons produced by using an amplification oligonucleotide that hybridizes to, and initiates polymerization from, an internal position of the target nucleic acid. Known sequencing methods include, for example, whole-genome sequencing as well as targeted sequencing wherein only subset of genes or regions of the genome are isolated and sequenced.

"SNARE-seq" means single-nucleus chromatin accessibility and mRNA Expression sequencing.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

Provided herein are methods for measuring chromatin accessibility and RNA expression in the same single cells at a very high throughput.

The disclosure provides a method for concurrent characterization of gene expression levels and epigenetic landscape within a single cell comprising determining chromatin accessibility and RNA expression in the cell with a splint oligonucleotide.

In embodiments, the invention provides the determining step further comprises genetic sequencing of chromatin accessible regions isolated from a micro-droplet.

In embodiments, the invention provides using barcoded oligonucleotide primers that facilitate digital counting of chromatin accessible regions in single cells for the determining step.

In embodiments, the invention provides characterizing a transcriptome from the cell's gene expression level and epigenetic landscape.

In embodiments, the invention provides characterizing an epigenetic regulatory landscape from the cell's gene expression level and epigenetic landscape.

In embodiments, the invention provides the splint oligonucleotide comprises a 5' complimentary region of adapter sequence and a 3' poly(A) tail.

In embodiments, the invention provides the determining step further comprises: (a) labeling chromatin open regions by ATAC-seq assay in the cell's intact nucleus using Tn5 transposase; (b) combining a splint oligonucleotide and barcoded oligo-dT beads in a lysis buffer; (c) co-encapsulating the nucleus and barcoded oligo-dT beads in the lysis buffer to form a plurality of droplets; (d) heating the droplets to release Tn5 transposase; (e) cooling the heated droplets; (f) retrieving barcoded beads from the cooled droplets; (g) subjecting the retrieved barcoded beads to gap filling/ligation of chromatin and reverse transcription of mRNA; and (h) preparing single nucleus chromatin and RNA sequencing libraries by detecting the barcoded beads.

In embodiments, the invention provides the splint oligonucleotide comprises a 33 bp complementary region of adapter sequence inserted by Tn5 polymerase at the 5' end, and a 30 bp poly(A) tail at the 3' end.

In embodiments, the gap filling/ligation of chromatin and reverse transcription of mRNA is concurrent, happening at the same time.

In embodiments, the invention provides characterizing an epigenetic control of gene expression.

In embodiments, the invention provides characterizing a cellular heterogeneity in healthy or diseased tissues, wherein the diseased tissue is tumorigenic.

The disclosure further provides a splint oligonucleotide, comprising a 33 bp complementary region of adapter sequence inserted by Tn5 transposase at the 5' end, and a 30 bp poly(A) tail at the 3' end.

In embodiments, the invention provides compositions of matter comprising the various constructs described above, including the splint oligonucleotide and others.

The disclosure further provides a method of sorting nucleic acids in a single cell comprising barcoding oligonucleotide-dT primers to provide unique molecular identifier sequences that facilitate digital counting of chromatin open sites in the cell, and sorting the sequenced samples into sample libraries by detection the barcoding.

RNA sequencing of single cells or nuclei can reveal their transcription state, while chromatic accessibility sequencing would uncover the associated upstream transcriptional regulatory landscape. Current strategies for high-throughput profiling these modalities separately requires significant integrative computational strategies[1,2] that may not fully recapitulate the true biological state. As such, their joint profiling within the same cells would enable the direct matching of transcriptional regulation to its output, allowing for more accurate reconstruction of the molecular processes underlying a cell's physiology. To enable highly parallel profiling of chromatin accessibility and mRNA from individual nuclei, the SNARE-seq technique was developed and implemented on a micro-droplet platform[3]. In this method, the accessible chromatin in permeabilized nuclei are captured by the Tn5 transposase, prior to droplet generation. Without heating or detergent treatment, binding of transposases to its DNA substrate after transposition can maintain the contiguity of the original DNA strands[4], allowing for the co-packaging of accessible genomic sites and mRNA from individual nuclei in the same droplets.

As such, the invention provides a splint oligonucleotide with sequence complementary to the adapter sequence inserted by transposition (5' end) and the poly A bases (3' end) allowing capture by oligo-dT-bearing barcoded beads. After encapsulation of nuclei, their mRNAs and fragmented chromatin can be released by heating the droplets, allowing access to splint oligos and adaptor coated beads having a shared cellular barcode (FIG. 1a). A pair of RNA-seq and chromatin accessibility libraries can be generated for sequencing (see Methods). The resulting data can then be connected by their shared cellular barcodes, without the need for probabilistic mapping of single-cell clusters from separate analyses. While SNARE-seq shows similarities to sci-CAR[5] conceptually, the method can be implemented on a more widely accessible Drop-seq platform and provides denser chromatin information due to a different design that captures chromatin information first, then linking it to the transcriptome.

Figure 3:
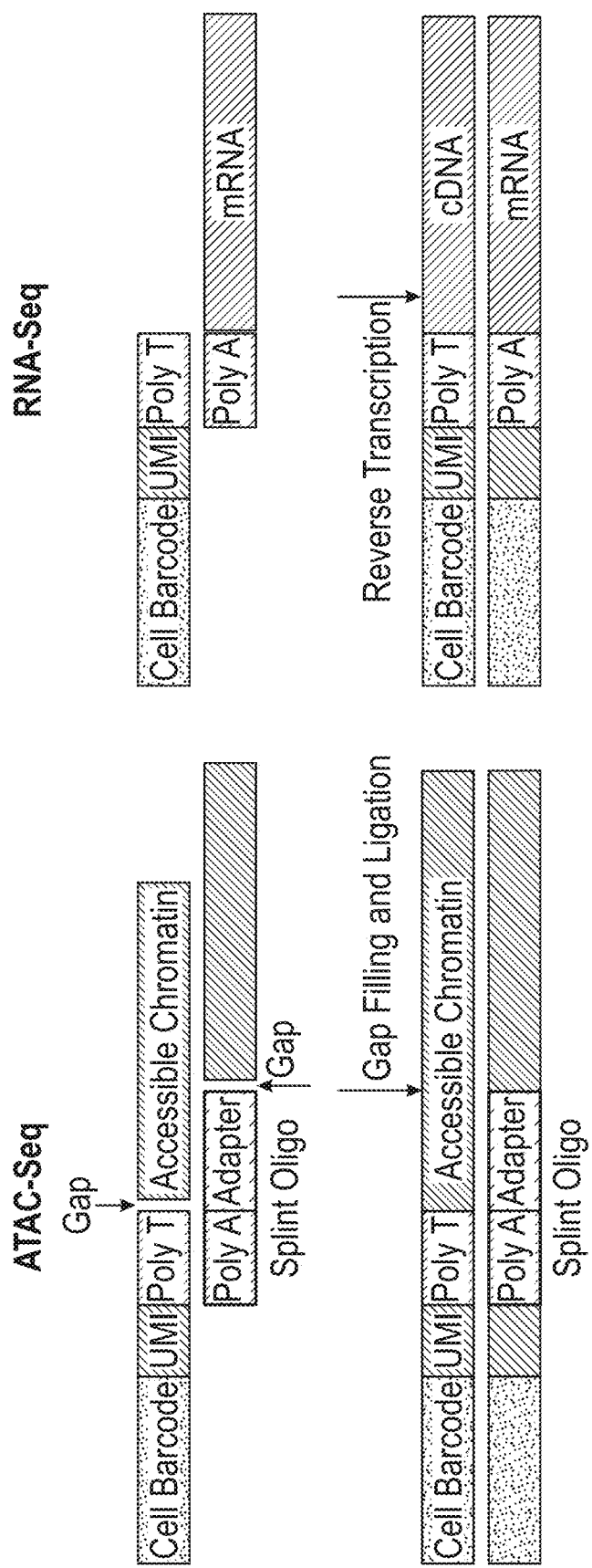
FIG. 3 depicts a cellular indexing of accessible chromatin regions and cDNA.

The workflow of SNARE-seq is illustrated in FIG. 1a. Chromatin open regions were first labeled by ATAC-seq assay on intact nuclei using hyperactive Tn5 transposase, followed by, co-encapsulation with a splint oligo, bearing a 33 bp complementary region of adapter sequence inserted by Tn5 at the 5' end, and a 30 bp poly(A) tail at the 3' end, single nucleus, and barcoded oligo-dT beads into a plurality of droplets. The droplets were heated at 72° C. to release Tn5 binding from chromatin and then cooled to allow oligo annealing and chromatin capture. Barcoded beads bearing dual-omic information were retrieved from the droplets, and subjected to gap filling/ligation and reverse transcription to add cellular index to chromatin and cDNA respectively (FIG. 3). Following initial pre-amplification of captured fragments, single nucleus chromatin and RNA sequencing libraries were prepared separately.

The size distribution of Tn5 cut fragments in SNARE-seq not only demonstrated clear nucleosome packing information, but also showed a 10 bp periodical pattern, reflecting the helical nature of double-stranded DNA.

Using a previously characterized locus in GM12878 lymphoblastoid cells, SNARE-seq results was shown to have a signal-to-noise ratio similar to that of ATAC-seq, with most, if not all, peaks overlapping those previously identified by ATAC-seq. Furthermore, the clustering result of SNARE-seq RNA-expression datasets generated from brain cortex nuclei samples along with previous snDROP-seq datasets (Lake BB et. al, Integrative single-cell analysis of transcriptional and epigenetic states in the human adult brain. Nat. Biotechnol. 2018 January; 36(1): 70-80) showed clear separation of multiple neuronal (In1-8 and Ex1-8) and non-neuronal (astrocyte (Ast), oligodendrocytes (oli), and oligodendrocyte progenitor cells (OPC)) groups.

One exemplary aspect of the present invention is the design of a splint oligo, which bears a 33 bp (±5 bp) complementary region of adapter sequence inserted by Tn5 transposase at the 5' end, and a 30 bp (±5 bp) poly(A) tail at the 3' end. The splint oligo is configured to help bridge barcoded oligo-dT primers and cut open chromatin together under low incubation temperatures in order to allow DNA annealing. By bridging barcoded oligo-dT primers and cut open chromatin, the splint oligo facilitates the capture of DNA fragments representing both chromatin accessibility and RNA expression.

A second exemplary aspect of the present invention is leveraging the ability of Tn5 transposase to maintain extensive contiguity of the original DNA molecules. Given the tight binding of Tn5 to its DNA substrate after transposition, accessible chromatin regions from single cells can be well-preserved before delivery into individual droplets. The accessible chromatin regions can then be captured by releasing Tn5 from DNA inside droplets through heating. This connects the molecular information of chromatin accessibility and RNA expression within the same microdroplets, thereby enabling simultaneous profiling of accessible chromatin and mRNA from single cells without the need for any laborious and error-prone separation steps.

Another exemplary aspect of the present invention is the use of the barcoded oligo-dT primers which provide unique molecular identifier (UMI) sequences that facilitate digital counting of chromatin open sites in single cells, and/or sorting the sequenced samples into sample libraries via detection of the appropriate barcode.

EXAMPLE

Figure 1B:
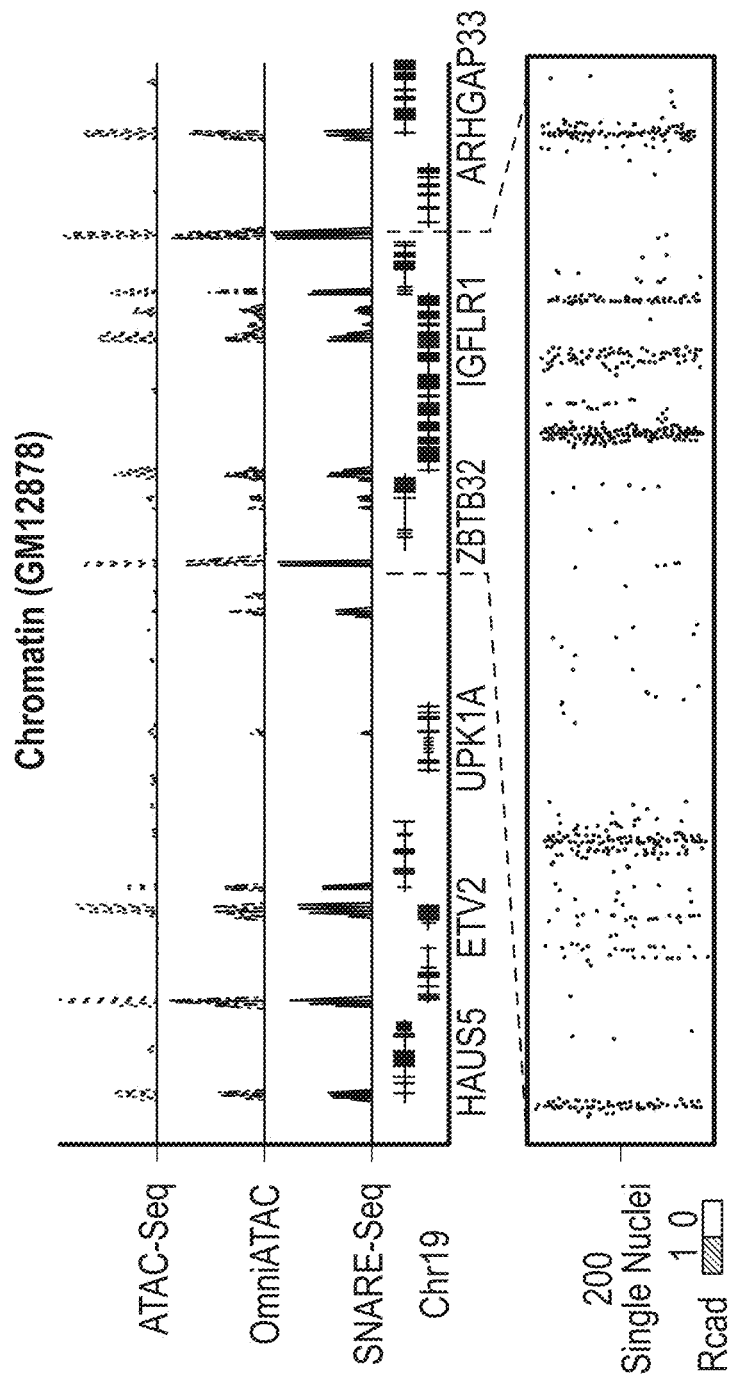

SNARE-seq, a Method for Connecting Chromatin Accessibility and Transcriptome in the Same Single Cell Assay To evaluate SNARE-seq's ability to capture accessible chromatin, a proof-of-principle experiment was performed on GM12878 cells, which have extensively characterized chromatin landscapes. Ensemble profiles of SNARE-seq accessibility data showed a signal-to-noise ratio similar to ATAC-seq[6] and Omni-ATAC7 (FIG. 1b). The aggregate SNARE-seq data also showed the expected periodical nucleosome pattern and a strong enrichment of fragments within canonical promoter regions, which are typical characteristics of bulk ATAC-seq data. The peaks called from the SNARE-seq data were validated by overlapping them with those of published bulk ATAC-seq and Omni-ATAC data[6] and found that 85.9% of ATAC-seq peaks were shared among all three assays, and that 87.6% of Omni-ATAC peaks were shared between Omni-ATAC and SNARE-seq. After filtering out low quality data, a median of 2720 accessible sites per nuclei was obtained, which compared favorably with most other single cell/nuclei ATAC-seq methods.

Figure 1C:
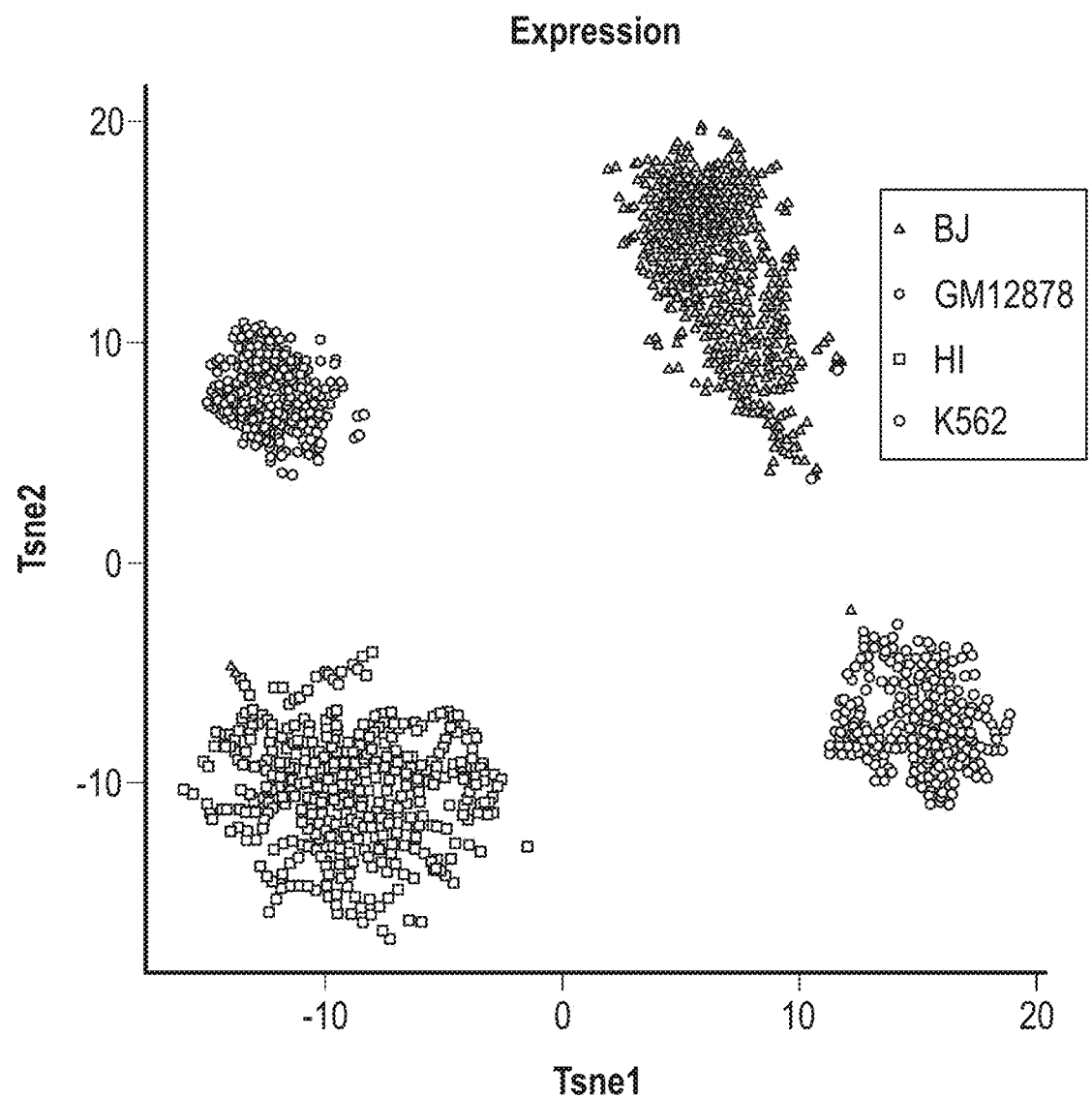
Figure 1D:
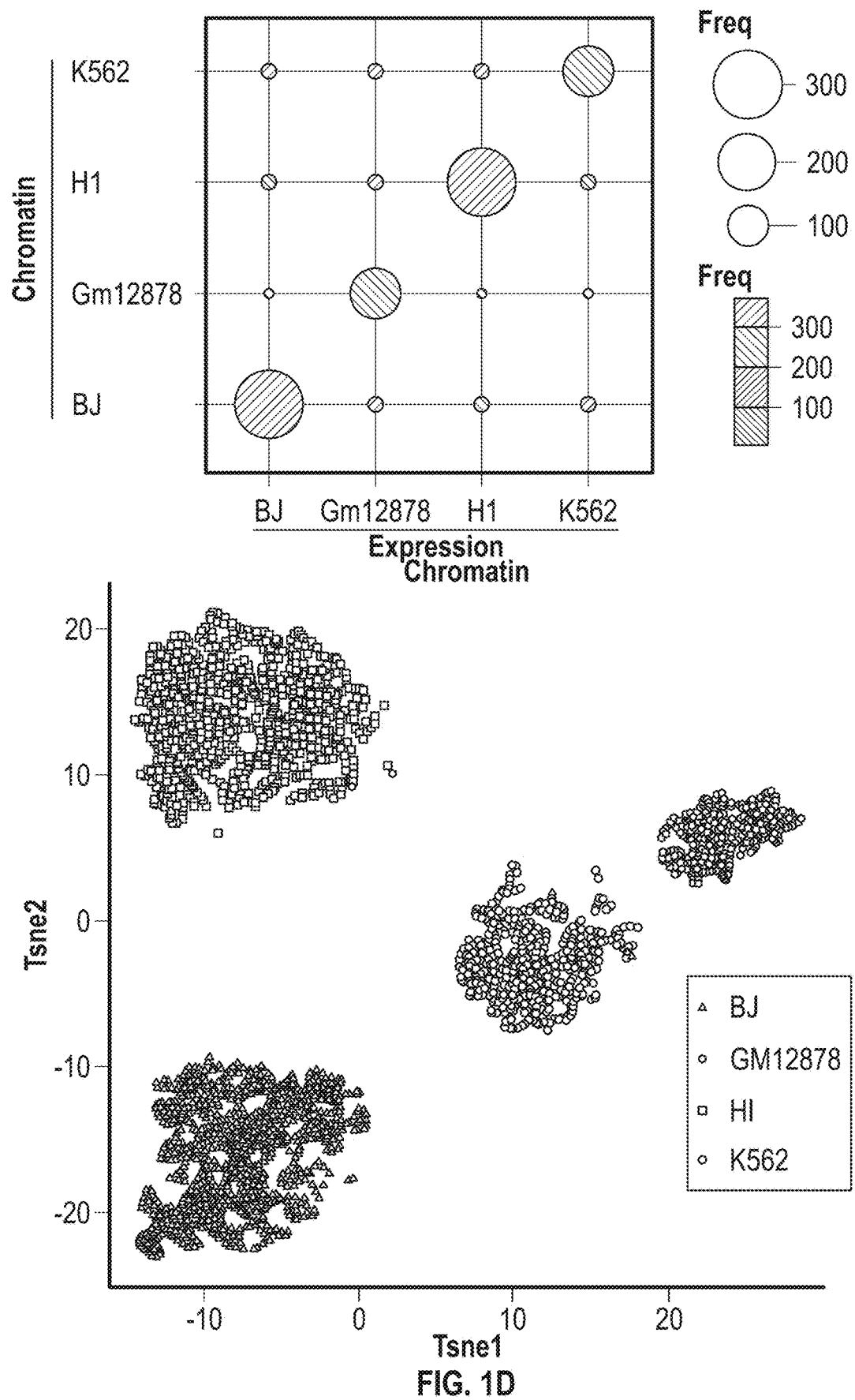

To assess the accuracy of SNARE-seq in identifying cell types, SNARE-seq was performed on mixtures of cultured human BJ, H1, K562 and GM12878 cells, and collected 1,047 paired profiles (median 500 UMIs; median 805 accessible sites). Separate clustering of expression and chromatin accessibility data showed clear separation into four distinct clusters (FIG. 1c). Differential expression of maker genes validated these cluster identities and classification results from both profiles were in good agreement (kappa coefficient of 0.92, FIG. 1d). Notably, it was found that transcription factors JUN, IRF8, POU5F1 and GATA1, which showed enriched expression in BJ, GM12878, H1 and K562 cells, respectively, also showed a similar pattern of preferential binding to chromatin sequences captured by SNARE-seq accessibility assay, consistent with previous observations[8]. Therefore, on a simple cell mixture model, SNARE-seq can effectively separate cell types based on both their chromatin signatures and transcriptomes, and at a high level of concordance.

Next SNARE-seq was applied to cerebral cortex from mouse brain (postnatal day 0, n=5) and recovered 5,081 nuclei that had both transcriptome (median 357 UMIs) and chromatin accessibility (median 2,583 accessibility sites) data after QC filtering. Correlation analysis of expression or chromatin profiles demonstrated great reproducibility between independent SNARE-seq experiments. Among all RNA reads, 94% aligned to the genome, with 37% of these mapped to exons and 42% mapped to introns, reflecting the enrichment of nascent transcripts in the nucleus. In comparison, despite a similar mapping rate (>91%), the chromatin accessibility data showed a larger fraction of reads (34%) mapped to intergenic regions. There was also enrichment of accessibility reads in close proximity to the transcription start site (10%) and low coverage in exons, suggestive of enhancer and promoter sequences present in those noncoding regions. Therefore, both RNA and chromatin reads had expected genome distributions, as previously observed from snDrop-seq[1] and snATAC data[9].

Figure 2A:
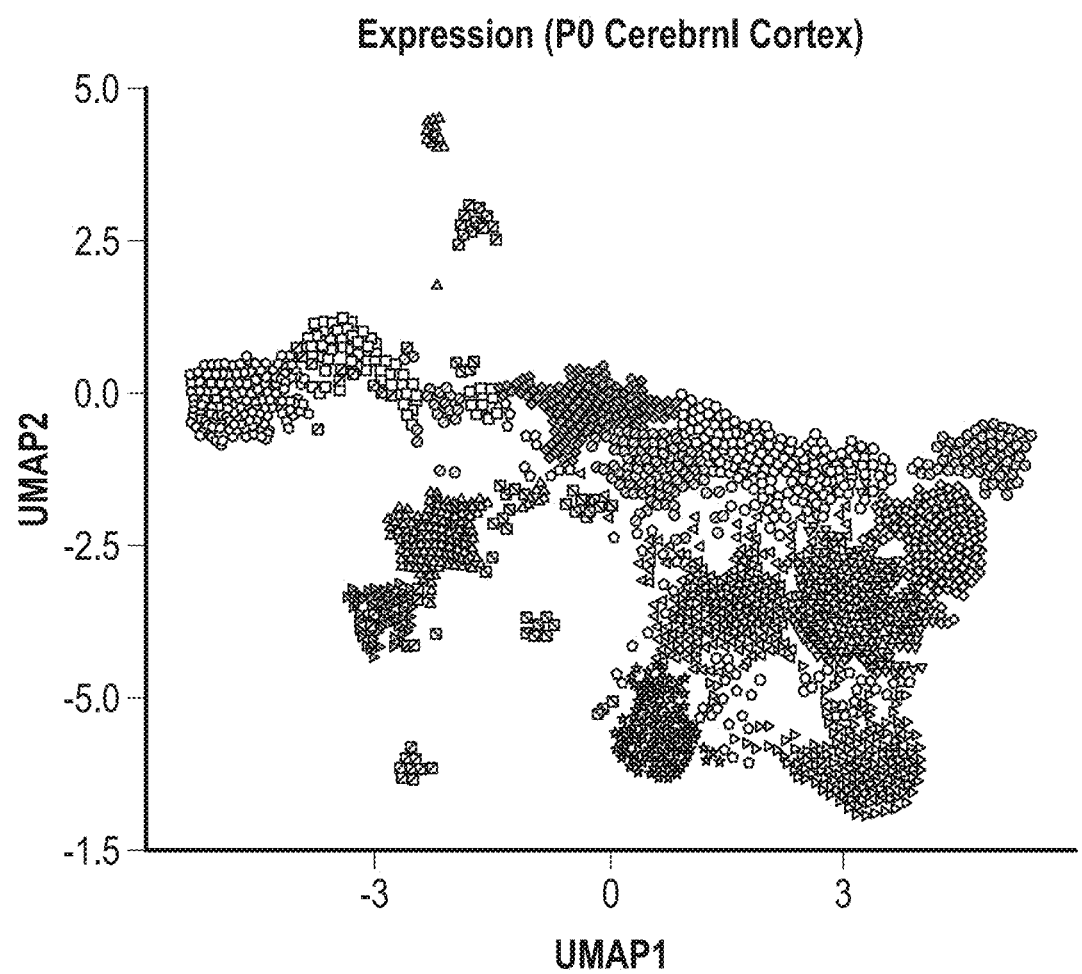
FIGS. 2a-2g show that SNARE-seq allows the linked profiling of single-cell transcriptome and chromatin accessibility on mouse postnatal cerebral cortex.
Figure 2B:
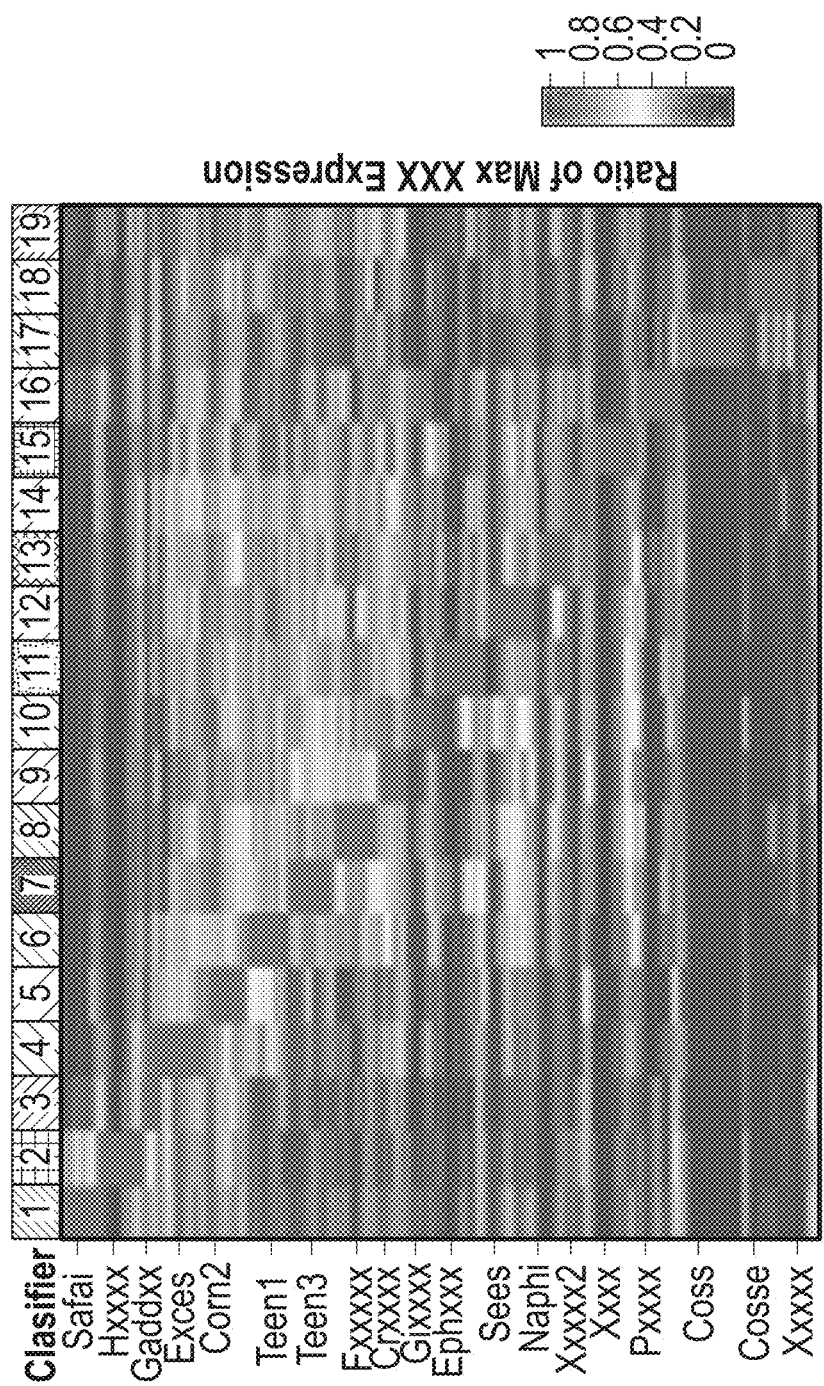

Unsupervised clustering of cerebral cortex transcriptomes identified 19 cell clusters, including: astrocytes/radial glia (Ast/RG); intermediate progenitor cells (IP); excitatory neurons (Ex); migrating inhibitory neurons (In); and Cajal-Retzius cells (CR). Several non-neuronal cell types were detected, including: oligodendrocyte progenitor cells (OPC); endothelial cells (End); pericytes (Peri); and microglia (Mic). These cell clusters ranged in size from 37 (0.7%) to 542 (10.7%) cells, and were independent of batch or sequencing depth. Uniform Manifold Approximation and Projection (UMAP) revealed a trajectory extending from the progenitor states reflective of the sequential development of cortical cell fates. Consistently, nuclei occurring adjacent to intermediate progenitors represented those of the late born neurons of the superficial layers (proceeding deep layer neurons) and glial cell types associated with the onset of gliogenesis that is expected at this time point (FIG. 2a). SNARE-seq transcriptome data was compared with a recently published single-cell RNA-seq dataset of the mouse cortex at a similar developmental time point that was generated by SPLiT-seq[10]. Despite a lower number of detected UMIs, the cell types and their signatures were reasonably well correlated. Notably, finer distinctions were captured between closely related cellular states and identified three sub-clusters of intermediate progenitor cells: cluster IP-Hmgn2, expressing Mki67, Top2a and Kif23 (FIG. 2b), representing cycling progenitors; cluster IP-Gadd45g, which was enriched for Gadd45g, representing apical progenitors that exited from cell-cycle[11]; and cluster IP-Eomes, representing basal progenitors that show early commitment to the neuronal lineage. Cell-type and layer identities of clusters were further validated by expected expression of known marker genes and in situ staining of novel discovered makers (FIG. 2b).

Figure 2C:
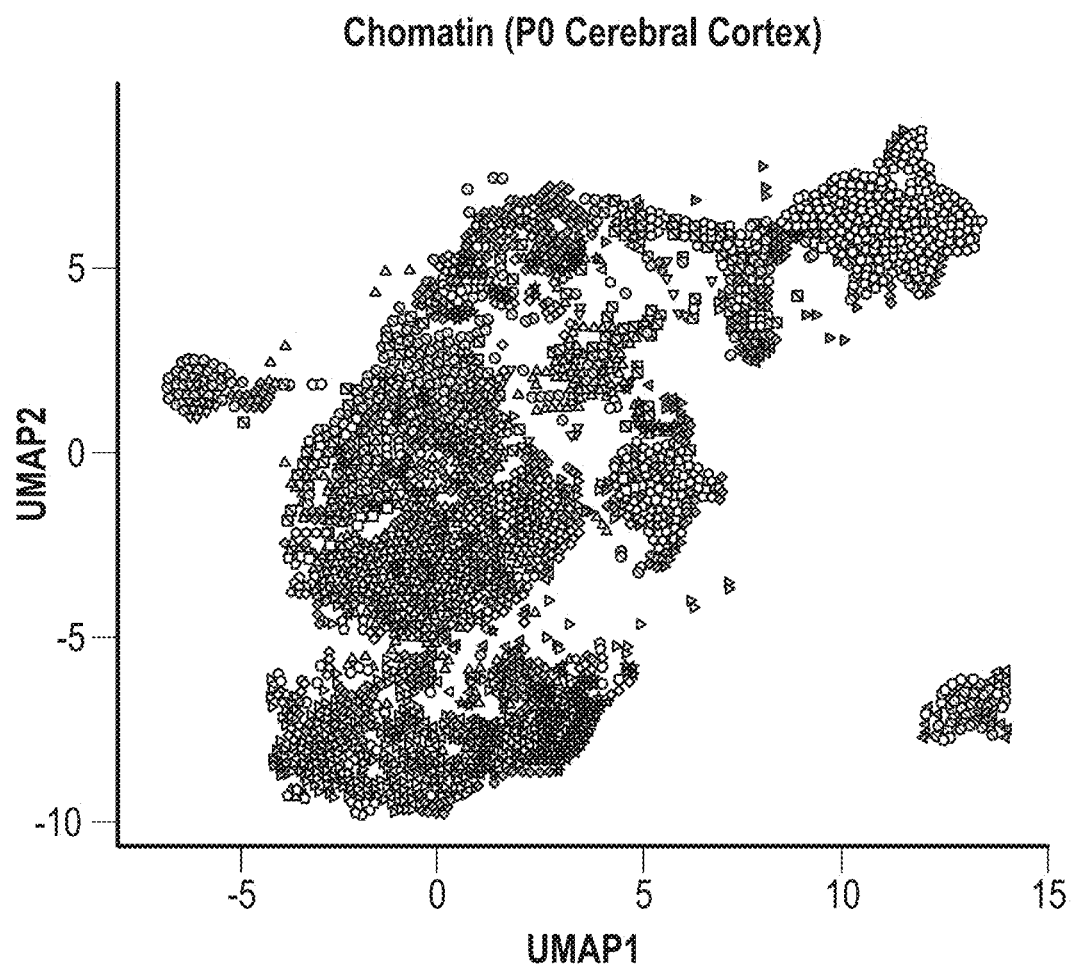

SNARE-seq chromatin accessibility profiles were compared with published bulk ATAC-seq ENCODE data on postnatal mouse brain cortex and found a strong concordance between these two methods. To cluster co-assayed cells based on their chromatin accessibility profiles, their corresponding transcriptional profiles were used to aggregate chromatin accessibility signals for each cluster separately, followed by peak calling and the probabilistic topic modeling method used in cisTopic12. After projecting onto lower dimensions using UMAP, most single-nuclei chromatin accessibility clusters (FIG. 2c), corresponded to the same cell types resolved from the corresponding expression data (FIG. 2a). Notably, the chromatin accessibility of deep layer excitatory neurons and migrating inhibitory neurons, which differentiated earlier in the cerebral cortex and ganglionic eminences, respectively, showed well-separated clusters, whereas those of late-generated superficial layer excitatory neurons were less distinct. This is likely due to the sparsity of chromatin data and/or dynamic epigenetic states that are still undergoing maturation. Cell-type identities of these clusters were further supported by the specific accessibility in the promoter region for marker gene loci Hes5 (Ast/RG), Gadd45g (IP), Meg3 (Neurons), Pdgfra (OPC), Vtn (Peri) and Apbblip (Mic). Importantly, it was found that the promoter accessibility of lineage markers Vtn and CD45 (for pericyte and microglia representing 1% and 0.7% of total cells) were present only in cell-type aggregated chromatin profiles that were identified de novo with transcriptome data. In contrast, chromatin data analyzed based on the accessible peaks called in batch-aggregated profiles, the current default strategy for sc-ATAC-seq data, was unable to detect these signals from background noise (FIG. 2e). Therefore, a priori knowledge of cell type identity in accessibility data using associated gene expression profiles permits more sensitive chromatin analysis. This underscores the strength of the SNARE-seq co-assay method over independent single-cell RNA and chromatin accessibility sequencing methods for detecting cell-type and subtype specific gene expression and regulation profiles.

Figure 2D:
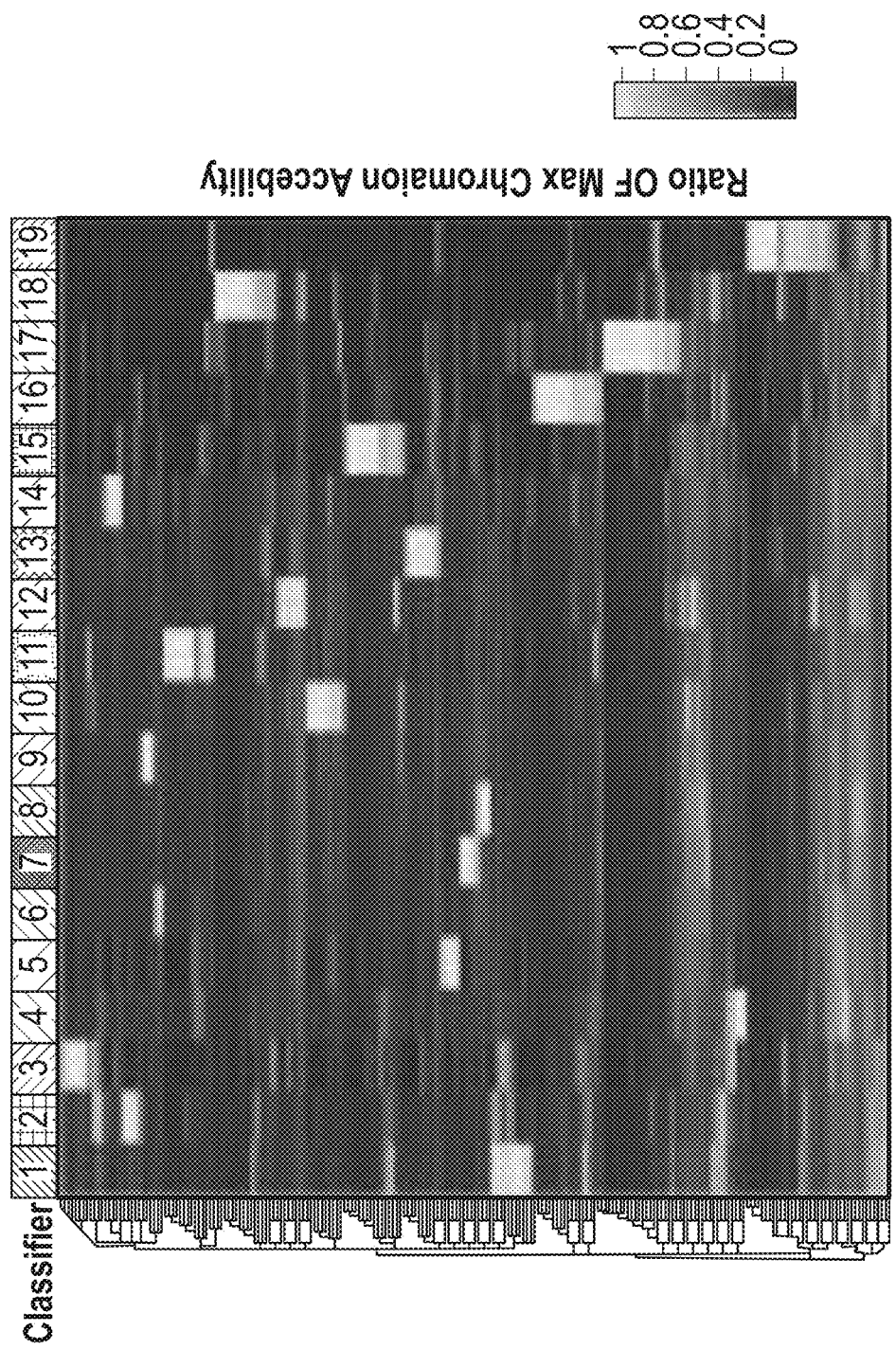
Figure 2E:
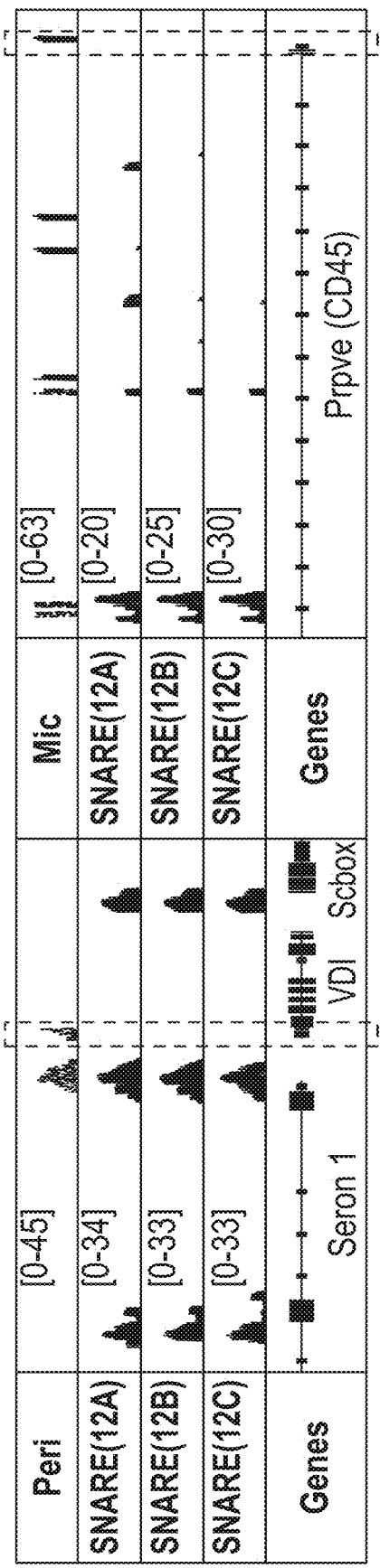

Differential accessibility (DA) test of SNARE-seq chromatin profiles identified 35,166 sites (p<0.05) across the 19 murine cerebral cortex cell types (FIG. 2d). Of all 35,166 differential accessible sites, 2,835 (8%) located within promoter regions, and 128 also showed differential gene expression between clusters. For theses 128 genes, the expression levels and their promoter accessibilities across all cell types were mostly positively correlated (median r 0.34), indicating direct linkage of chromatin accessibilities to the corresponding transcriptomes. To further characterize the DA sites, gene ontology enrichment and motif discovery analysis was performed using GREAT and HOMER, respectively. Notably, genomic elements that were mostly associated with Ast/RG and OPC cells fell into the biological processes regulating stem cell maintenance and differentiation. These sites were further enriched for binding motifs of LHX2 and SOX2, both of which are known regulators of neurogenesis and gliogenesis[13,14] It was determined that differential accessible sites of IP-Gadd45g (representing 1.9% of the total cells) were enriched for the Wnt signaling pathway components, consistent with the role or this pathway in regulating cell cycle exit and promoting neuronal differentiation of intermediate progenitors[15]. Therefore, linking chromatin accessibility profiles to transcriptomic data directly allowed effective identification of cell-type specific genetic regulatory mechanisms.

Figure 2F:
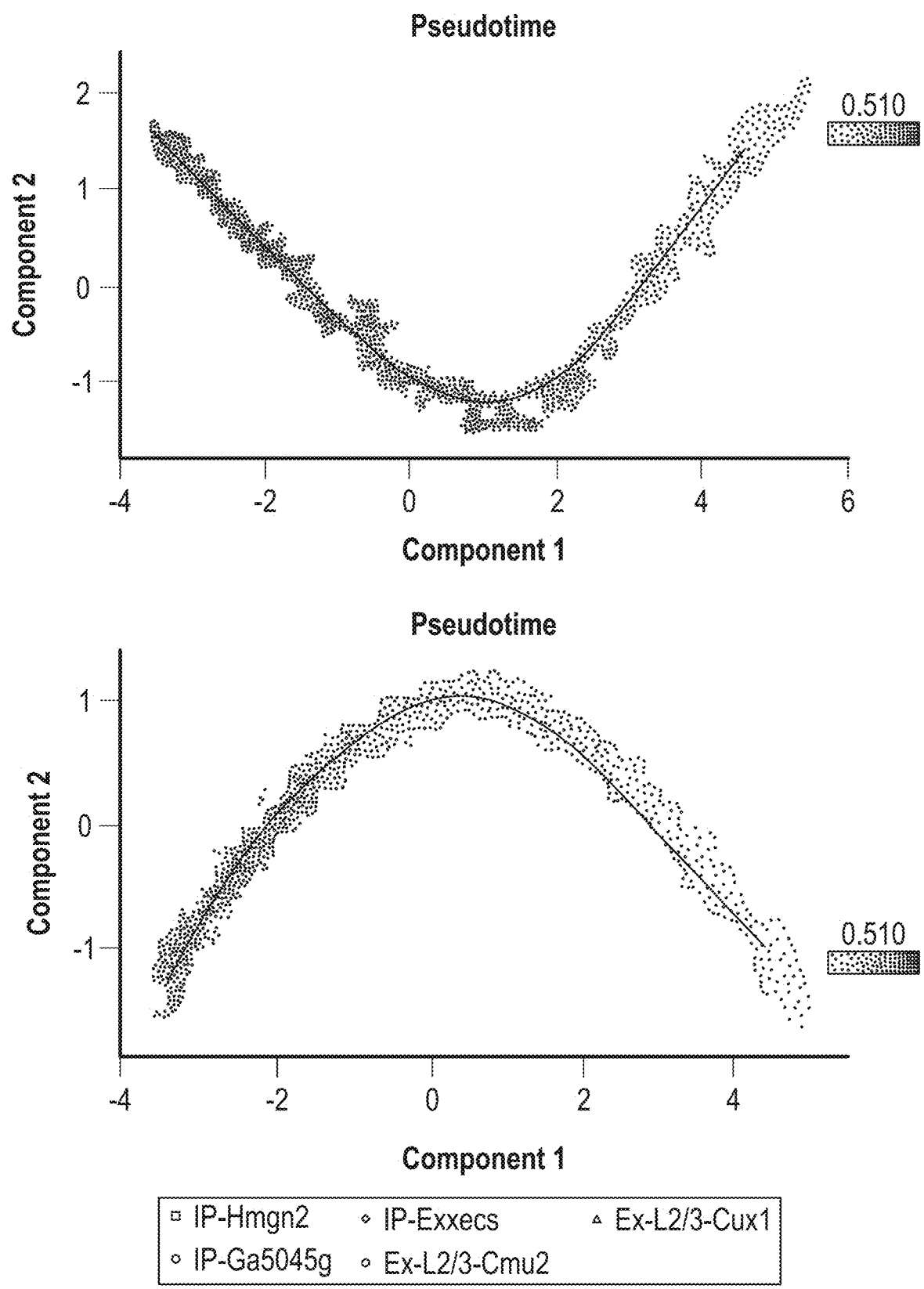
Figure 2F:
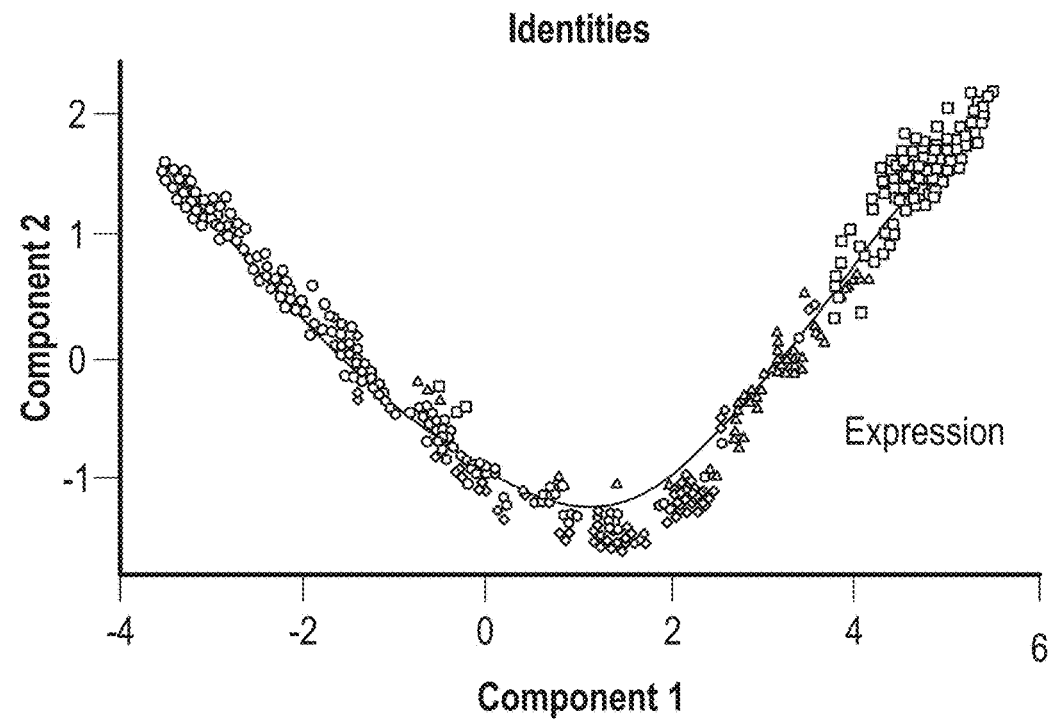
Figure 2F:
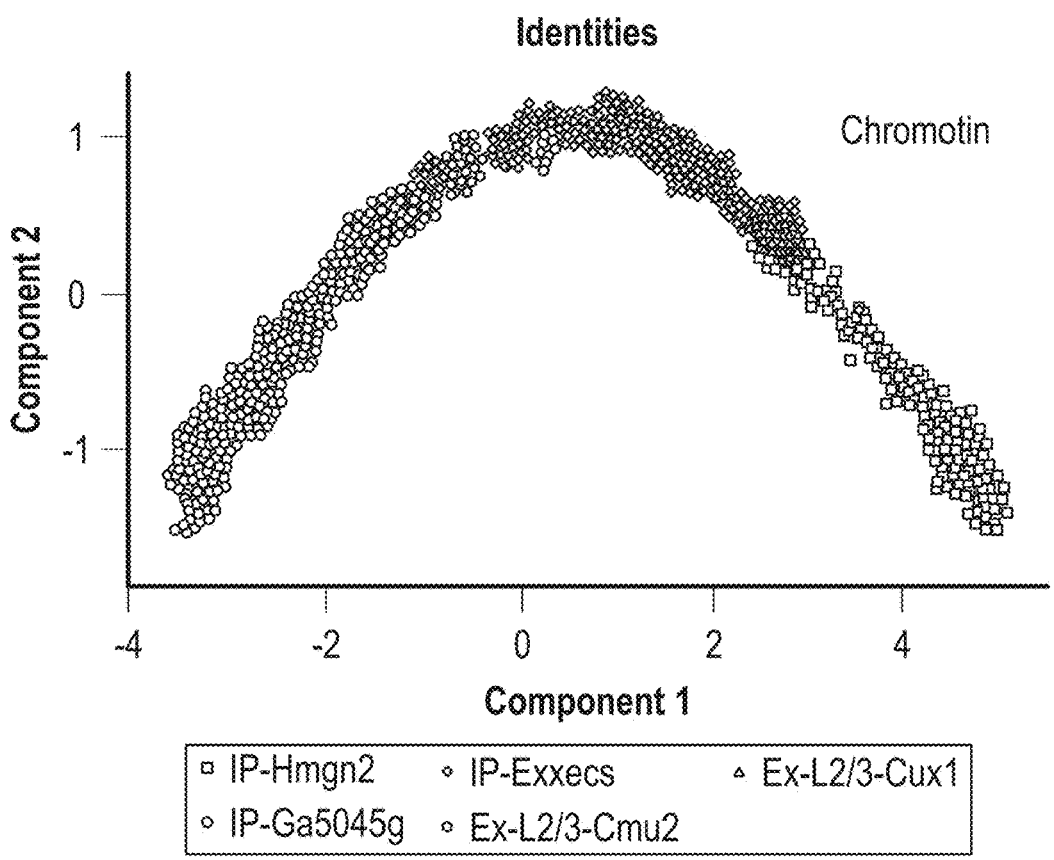
Figure 2G:
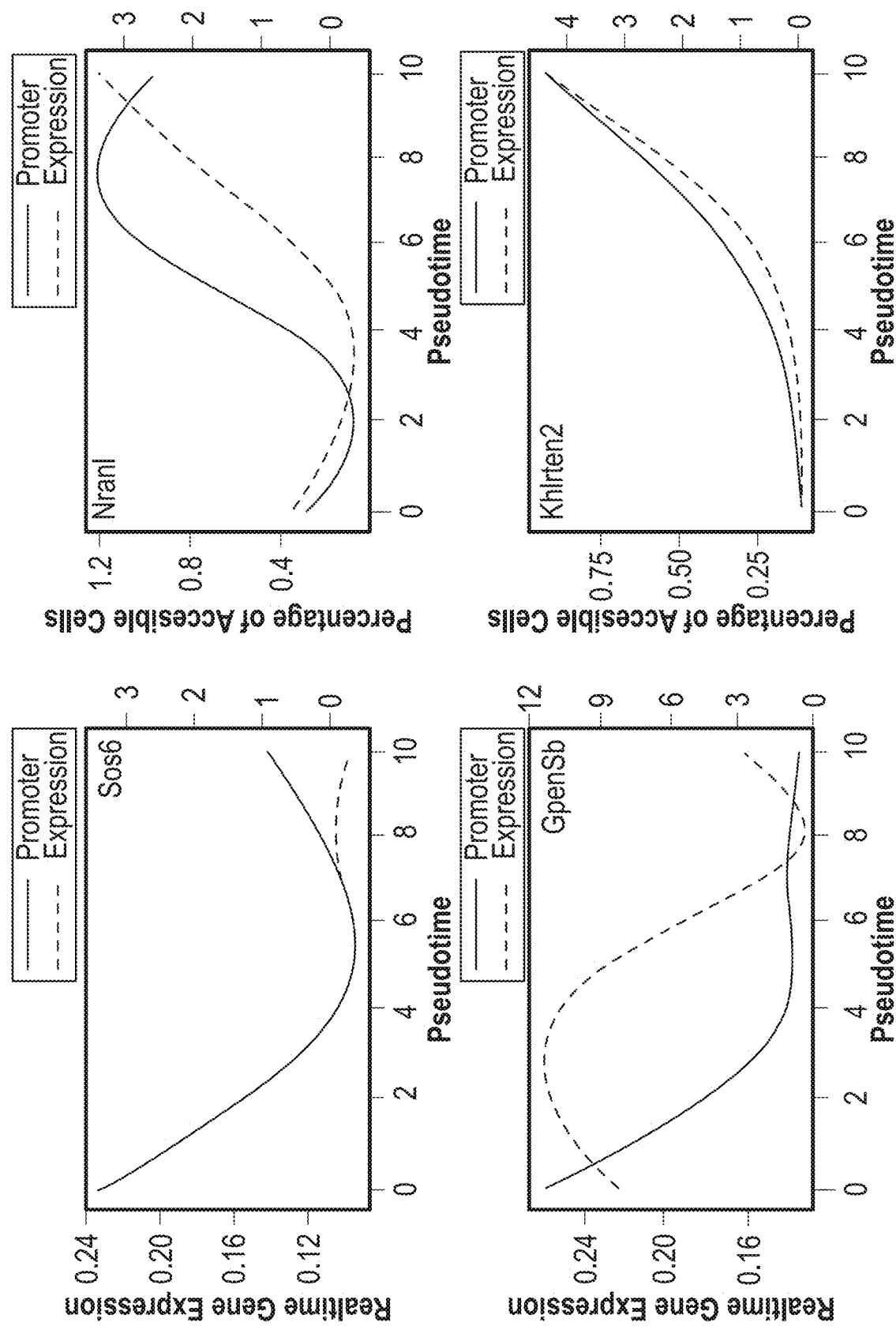

To further demonstrate the utility of having a direct linkage between transcriptome and chromatin accessibility, the transition of intermediate progenitors to upper layer excitatory neurons was reviewed. Using Monocle, gene-expression profiles of 1,469 nuclei were obtained along a pseudotime trajectory based on the top differential expressed genes (qval<0.05, FIG. 2f, upper panel). From transcription kinetics, a clear pattern was obtained originating from a cell-cycle exited state (Mki67 and Gadd45g), that progressed from neuroblast stages (Eomes and Unc5d) to Foxpl and Cuxl-expressing upper layer neurons[16,17] Accessibility profiles of the same nuclei were oriented along a separate trajectory (FIG. 2f, lower panel) based on a set of 1,332 sites that showed differential accessibility (qval<0.1). Notably, these separately constructed developmental trajectories showed high correlation (r=0.87) along pseudotime. From these differential accessible sites, 103 were found within promoter regions and 21 associated genes were also differentially expressed by pseudotime. Intriguingly, most of these genes presented similar directional changes in promoter accessibility and expression level. For example, Sox6, a transcription factor which is required for maintenance of neural precursor cells[18], and membrane protein-encoding Mlc1 showed a decline along neuronal differentiation, while Khdrbs2 (SLM1), an RNA-binding protein participating in alternative splicing, and its regulating target Nrxnl[19] showed similar directional raise along neurogenesis. Thus, SNARE-seq provided linked expression and chromatin accessibility profiles that enables construction of regulatory dynamics during developmental programs.

Overall, SNARE-seq is a robust method allowing the joint measurement of transcriptome and chromatin accessibility in single cells or nuclei. Due to a simple design that does not rely on proprietary reagents, SNARE-seq can be widely implemented. Compared to the recently reported sci-CAR[5], SNARE-seq showed more accessible sites (4~5 times), which improved the discovery of differentially accessible sites by ~2-fold and provided a much better separation of cell clusters. Note that SNARE-seq captures less transcripts (2~3 times) per cell, potentially due to some level of RNA degradation during chromatin tagmentation. However, since the transcriptome is highly cell-type specific, having fewer RNA reads per cells did not reduce the number of cell clusters identified. The recovery of RNA molecules could be further improved by gentle nuclei fixation[10,28]. Finally, the throughput of this assay may potentially be further improved through an integration with a cellular combinatorial indexing strategy). SNARE-seq represents a valuable tool for the study of tissue complexity on both the inputs and outcomes of transcriptional regulation information, and is especially useful for creating cell atlases of human tissues and clinical samples.

Ethics. The human embryonic stem cell line H1 was purchased from WiCell and the related study was approved by UCSD Embryonic Stem Cell Research Oversight (ES-CRO) Committee.

Cell culture. BJ and K562 cells were maintained in DMEM medium supplemented with 10% fetal bovine serum. GM12878 cells were maintained in 1640 medium supplemented with 15% fetal bovine serum. H1 human embryonic stem cell line was maintained in feeder-free mTeSR medium and passaged with ReLeSR according to manufacturer's instruction.

Nuclei preparation. GM12878 nuclei were extracted with ATAC-Resuspension Buffer containing 0.1% NP40, 0.1% Tween-20, and 0.01% Digitonin as described previously[4]. Nuclei from human cell line mixture were extracted with nuclear extraction buffer (NEB) (0.32 M sucrose, 5 mM CaCl2, 3 mM Mg(Ac)2, 0.1 mM EDTA, 20 mM Tris-HCl (pH=8), and 0.1% Triton X-100). To extract nuclei from mouse cerebral cortex (C57BL/6 mouse cortex at postnatal day 0, purchased from BrainBits (Cat #C57PCX)), the pair of tissue samples were chopped into small pieces with a razor blade and were homogenized using a glass Dunce tissue grinder (10 times with pastel A and 20 times with pastel B) in 2 ml ice-cold Nuclei EZ Prep buffer (Cat #NUC101). Nuclei were then passed through a 30-p.m filter (Sysmex Partec), spun down for 10 mM at 900 g, and then washed and resuspended in PBS supplemented with 1% fatty-acid-free BSA.

Tn5 tagmentation of nuclei. Nuclei were counted with an automated cell counter and approximately 200,000 nuclei were used for tagmentation. Nuclei pellets were resuspended in a total of 50 μL reaction mix containing 25 μL 2X Nextera Tagment DNA Buffer, 8 μL TDE1 Tagment DNA Enzyme and 1 μL RNase inhibitor and incubated at 37° C. for 30 min with shaking at 500 rpm. After tagmentation, nuclei were resuspended and washed with PBS containing 1% BSA and kept on 4° C. until droplet generation.

Nuclei barcoding. Droplet generation was performed as described previously[2], with a few modifications. Briefly, tubing and syringes were coated with 1% BSA to prevent nonspecific binding and then rinsed with PBS prior to experiment. Ficoll PM-400 was added in nuclei suspension buffer instead of lysis buffer to mitigate nuclei settling. To capture released chromatin fragments with barcoded beads, 1 μL splint oligo (Nextera-R1-rc-polyA, 10 μM) was added into Drop-seq lysis buffer. Nuclei suspension at a concentration of 100 nuclei/μl were co-encapsulated with barcoded beads (from ChemGenes, Cat #Macosko201110) in droplets. When encapsulation was complete, microfluidic emulsion collected in Falcon tubes were overlaid with a layer of mineral oil and then transferred to a 72° C. water bath to lyse nuclei and release binding of Tn5 with genomic DNA. After 5 minutes of incubation, collection tubes were moved from the water bath to ice.

Tn5 tagmentation of nuclei. Nuclei were counted with an automated cell counter and approximately 200,000 nuclei were used for tagmentation. Nuclei pellets were resuspended in a total of 50 μL reaction mix containing 25 μL of tagmentation buffer (2X NEXTERA® Tagment DNA Buffer), 8 μL TDE1 Tagment DNA Enzyme and 1 μL RNase inhibitor and incubated at 37° C. for 30 min with shaking at 500 rpm. After tagmentation, nuclei were resuspended and washed with PBS containing 1% BSA and kept on 4° C. until droplet generation.

Nuclei barcoding. Droplet generation was performed as described previously, with a few modifications. Briefly, tubing and syringes were coated with 1% BSA to prevent nonspecific binding and then rinsed with PBS prior to experiment. Ficoll PM-400 was added in nuclei suspension buffer instead of lysis buffer to mitigate nuclei settling. To capture released chromatin fragments with barcoded beads, 1 μL splint oligo (NEXTERA®-R1-rc-polyA, 10 μM) was added into Drop-seq lysis buffer. Nuclei suspension at a concentration of 100 nuclei/μl were co-encapsulated with barcoded beads (from ChemGenes, Cat #Macosko201110) in droplets. When encapsulation was complete, microfluidic emulsion collected in Falcon tubes were overlaid with a layer of mineral oil and then transferred to a 72° C. water bath to lyse nuclei and release binding of Tn5 with genomic DNA. After 5 minutes of incubation, collection tubes were moved from the water bath to ice.

Sequencing library preparation. Droplets were broken by perfluoro-octanol, after which beads were harvested and washed with 6X SSC containing 10 μL blocking oligos (NEXTERA®-R1-bk and NEXTERA®-Ad2-bk, 100 μM). After washing beads with 6X SSC again and RT buffer once, beads were resuspended in 200 μL reverse transcription/ ligation mix (2X T7 ligation buffer, 50 mM KCl, 2% Ficoll, 1 nM dNTP, 2.5 pM Template Switch Oligo, 10 mM DTT, 5 μl RNase inhibitor, 12.5 μL Hemo Klentaq, 2.5 μL T7 ligase and 2.5 μL reverse transcriptase), and incubated at room temperature for 30 minutes and at 42° C. for 90 minutes, followed by treatment with Exonuclease I at 37° C. for 45 minutes. Then an aliquot of 10,000 beads were spun down and library was then PCR amplified using primer pair NEXTERA®-R2/Tso-PCR for a total of 16 cycles. After column purification, PCR products were split into two halves for either cDNA or chromatin library amplification. To prepare the cDNA sequencing library, 0.6X bead size selected PCR products were amplified with primer Tso-PCR alone to enrich cDNA library, following by another round of 0.6X bead size selection. Sequencing libraries were constructed with a DNA library preparation kit (NEXTERA®Nextera XT kit) as described previously[2]. To prepare the chromatin sequencing library, primer pair P5XX-Tso/Ad2.X were used to add indexes and P5/P7 sequences, and the DNA library with fragment sizes between 225 to 1000 bp was carefully excised from PAGE gel and purified using column purification.

Sample correlation analyses. For expression data, Pearson correlation was calculated with log normalized transcriptional reads aggregated by samples. For chromatin data, pairwise genomic read coverage was calculated using multiBamSummary with consecutive bins of equal size (10 kb) across genome, and the resulting correlation matrices were used to compute the overall similarity between samples.

Expression data clustering. For human cell line mixture, barcodes with fewer than 200 UMIs or more than 2,000 UMIs were omitted, and barcodes with both transcriptome and chromatin accessibility profiles were selected. The expression count matrix was then normalized in PAGODA2 package. Winsorization procedure was employed to cap the magnitude of the ten most extreme values for each gene. Variance of each gene was modeled as dependency on the expression magnitude (log scale) as a smoothed generalized additive model with smoothing term k=10 (mgcv package in R). The observed-to-expected variance ratio for each gene was modeled by F distribution using the degrees of freedom corresponding to the number of successful gene observations. To normalize the contribution of each gene in the subsequent principal component analysis, we rescaled the variance of each gene to match the tail probability obtained from the F distribution under a standard normal sampling process. Cell clusters were determined from an approximate k-nearest-neighbors graph based on a cosine distance of the top 10 principal components derived from the top 1,000 variable genes from the variance-adjusted expression matrix, using the Infomap community detection algorithm (as implemented in the igraph R package). Cell clusters were visualized by ^-distributed stochastic neighbor embedding (t-SNE). For mouse cerebral cortex experiments, 6663 barcodes with more than 200 UMIs and less than 1200 UMIs were retained, and 5488 (82.4%) barcodes were left after a second round filtering to remove those with fewer than 250 accessible sites and fraction of reads in peak lower than 0.4. The expression count matrices were combined across independent experiments and were batch corrected, and normalized in PAGODA2 package. Expression variance was adjusted as aforementioned. Then top 2,000 variable genes were used to derive top 50 principal components, and cell clusters were determined from KNN graph. Cell clusters with fewer than 25 cells were omitted from further analysis and resulting 5081(76.3%) cells were re-clustered and visualized by UMAP projection on the top 20 principal components. Genes that were differentially expressed between cell types were identified using Wilcoxon rank sum test in Seurat (v2.3.4). Cell clusters were annotated manually on the basis of known markers for the cerebral cortex and gene expression pattern from DropViz.

Comparison of SNARE-seq expression data with SPLiT-seq data. Top 20 genes from the statistically significant principal components differentiating cell types, as well as the top 50 differentially expressed genes associated with each cell type, were identified by Seurat and cluster-averaged expression values were used for correlation analysis between SNARE-seq P0 and SPLiT-seq P2 mouse cerebral cortex expression dataset.

Cell Cycle Phase Assignments. Each cell was scored using CellCycleScoring function in Seurat based on its expression of G2/M and S phase marker genes. Cells with high G2/M or S scores were assigned as G2/M phase or S phase respectively while cells expressing neither are assigned as G0/G1 phase.

Clustering of chromatin accessibility data. To cluster chromatin accessibility data from the human cell mixture, the count matrix was first binarized and peaks with fewer than overall 5 counts or expressing in more than 10% of cells were removed. Probability of a region-topic distribution and topic-cell distribution were calculated using latent Dirichlet allocation model with a collapsed Gibbs sampler in cisTopic (v0.1). The number of topics with the highest likelihood were picked and principal component analysis were performed for all topics and clustering was visualized by UMAP projection of PCA scores. For mouse cerebral cortex accessibility datasets, cell clusters identified by expression data were used and raw chromatin reads associated with barcodes from the same cell types were aggregated together and cluster-specific peaks were called with bulk ATAC-seq pipeline for each identified cluster. Peaks lists were then merged and the accessibility count matrices were generated by overlapping reads with the merged list. The accessibility count matrices were combined across experiments and clustering was done in a same way in cisTopic as aforementioned. Cell clusters were visualized by UMAP projection of the principal components scores of top 25 topics.

Identify differential accessible sites. To identify cluster-specific accessible sites, differential accessible probabilities (p-value) for each peak in each cluster were calculated using Fisher's exact test. P-values were then converted to q-values by the Benjamini-Hochberg procedure, and peaks with p-values lower than 0.05 in each cluster were kept. The cluster-specific peak counts per cell were then aggregated and normalized by cell-specific library size factors computed separately by estimateSizeFactorsForMatrix in Monocle (v2.10) and visualized using heatmap.

Developmental ordering of early neurogenesis subset. To order cells according to their developmental trajectory of early neurogenesis based on expression data, we selected 1,498 expression datasets for cells from the mouse cerebral cortex identified as IP-Hmgn2, IP-Gadd45g, IP-Eomes, Ex-L2/3-Cntn2 and Ex-L2/3-Cux1 by the previous PAGODA2 clustering- based approaches. Differentially expressed genes across cell types were identified with the differentialGeneTest function of Monocle and 503 most significant genes (qval<0.001) were retained to construct the pseudotime trajectory. Cells were ordered according to their value along the trajectory tree. The gene expression along pseudotime was calculated in the same way and genes passing significant test (qval<0.05) and gene expression kinetics were visualized using the plot_genes_in_pseudotime function in Monocle. Chromatin accessibility dynamics along pseudotime were calculated similarly with gene expression. Briefly, peaks within 10 kb distance were merged in Cicero and differential accessible sites across cell types were tested. After ranking accessible sites by significance (as reported by differentialGeneTest), the top 1,300 most significant sites were used to construct the pseudotime trajectory. To select the differentially accessible promoters along pseudotime, we first selected the differential accessible sites within 2 kb of a gene's transcriptional start site and intersected with the list of differential expressed genes obtained from the step above. Promoter accessibilities were then visualized with the plot_accessibility_in_pseudotime function in Monocle and a natural spline was used to fit the promoter accessibilities along pseudotime with percentage of accessible cells as a covariate.

Annotation of genomic elements. The GREAT algorithm was used to annotate differential accessible sites using the following settings: 1 kb upstream and 1 kb downstream, up to 500-kb max extension. The HOMER package (v4.10) was used to determine motif enrichment using default setting.

External data. Published Omni-ATAC (SRP103230), scATAC-seq (GSE65360), snATAC (GSE100033), SPLiT-seq (GSE110823), sci-ATAC(GSE68103), sci-CAR (GSE117089) and ATAC-seq (ENCODE) data were reprocessed. RNA in situ hybridization images for marker genes was taken from the Allen Institute Brain Atlas.

Data availability. Raw and processed data is available at Gene Expression Omnibus database under the accession number GSE126074.

These and other features and embodiments will be apparent to those skilled in the art without limitation by the disclosed embodiments.

REFERENCES

1. Lake B B. et al. *Nat Biotechnol* 36, 70-80 (2018).
2. Duren Z. et al. *Proc Natl Acad Sci USA* 115, 7723-7728 (2018).
3. Macosko E Z. et al. *Cell* 161, 1202-1214 (2015).
4. Amini S et al. *Nat Genet* 46, 1343-9 (2014).
5. Cao J. et al. Science 361, 1380-1385 (2018).
6. Buenrostro J D et al. *Nat Methods* 10, 213-8 (2013).
7. Corces M R. et al. *Nat Methods* 14, 959-962 (2017).
8. Zamanighomi M. et al. *Nat Commun* 9, 2410 (2018).
9. Preissl S. et al. *Nat Neurosci* 21, 432-439 (2018).
10. Rosenberg A B. et al. *Science* 360, 176-182 (2018).
11. Yuzwa S A. et al. Cell Rep 21, 3970-3986 (2017).
12. dx.doi.org/10.1101/370346.
13. Subramanian L. et al. *Proc Natl Acad Sci U S A* 108, E265-74 (2011).
14. Zhang S. et al. *Mol Neurobiol* 55, 9001-9015 (2018).
15. Harrison-Uy S J, Pleasure S J. *Cold Spring Harb Perspect Biol* 4, a008094 (2012).
16. Artegiani B. et al. *Cell Rep* 21, 3271-3284 (2017).
17. La Manno G. et al. *Nature* 560, 494-498 (2018).
18. Lee K E. et al. *Proc Natl Acad Sci USA* 111, 2794-9 (2014).
19. Iijima T. et al. *Cell* 147, 1601-14 (2011).
20. Chen X. et al. *Nat Methods* 13, 1013-1020 (2016).

What is claimed is:

1. A method for concurrent characterization of gene expression levels and epigenetic landscape within a single cell by determining chromatin accessibility and RNA expression in the cell, the method comprising:
   a) labeling chromatin open regions in the cell's intact extracted nucleus using Tn5 transposase to add an adapter sequence to the chromatin open regions;
   b) combining a splint oligonucleotide and barcoded oligo-dT beads comprising strings of deoxythymine in lysis buffer, wherein the splint oligonucleotide comprises a 5' region complementary to the adapter sequence and a 3' poly (A) tail;
   c) co-encapsulating the nucleus and barcoded oligo-dT beads in the lysis buffer to form a plurality of droplets;
   d) releasing the Tn5 transposase from genomic DNA within the droplets;
   e) retrieving barcoded beads from droplets after releasing the Tn5 transposase, wherein the retrieved barcoded beads comprise 1) mRNA from the cell annealed to the strings of deoxythymine and 2) the genomic DNA from the cell annealed via the adapter sequence to the splint oligonucleotide, wherein the splint oligonucleotide is further annealed to the strings of deoxythymine via the 3' poly (A) tail;
   f) subjecting the retrieved barcoded beads to gap filling/ligation of chromatin and reverse transcription of mRNA; and
   g) preparing single nucleus chromatin and RNA sequencing libraries by detecting the barcoded beads.

2. The method of claim 1, wherein further comprising: h) the determining chromatin accessibility by genetic sequencing of chromatin accessible regions isolated from at least one of the droplets.

3. The method of claim 2, wherein use of the barcoded oligo-dT beads facilitates digital counting of chromatin accessible regions in single cells in the determining step h).

4. The method of claim 3, further comprising characterizing an epigenetic regulatory landscape from the cell's gene expression level and epigenetic landscape.

5. The method of claim 1, wherein releasing the Tn5 transposase from the droplets comprises heating the droplets to release the Tn5 transposase from the genomic DNA.

6. The method of claim 1, wherein the 5' region of the splint oligonucleotide complementary to the adapter sequence inserted by Tn5 transposase comprises 33 complementary bases, and the poly (A) tail at the 3' end comprises 30 bases.

7. The method of claim 1, wherein the gap filling/ligation of chromatin and reverse transcription of mRNA is concurrent.

8. The method of claim 1, further comprising characterizing an epigenetic control of gene expression.

* * * * *